(12) United States Patent
Sereda et al.

(10) Patent No.: US 10,316,010 B2
(45) Date of Patent: Jun. 11, 2019

(54) VERSATILE NON-DESTRUCTIVE SURFACE MODIFICATION OF CARBONACEOUS MATERIALS AND PROCESS FOR GRAFTING INTO POLYMER MATRICES

(71) Applicant: South Dakota Board of Regents, Vermillion, SD (US)

(72) Inventors: Grigoriy Sereda, Vermillion, SD (US); Joseph Keppen, Sioux Falls, SD (US)

(73) Assignee: South Dakota Board of Regents, Pierre, SD (US)

( * ) Notice: Subject to any disclaimer, the term of this patent is extended or adjusted under 35 U.S.C. 154(b) by 44 days.

(21) Appl. No.: 15/383,935

(22) Filed: Dec. 19, 2016

(65) Prior Publication Data

US 2017/0233364 A1    Aug. 17, 2017

Related U.S. Application Data

(60) Provisional application No. 62/268,657, filed on Dec. 17, 2015.

(51) Int. Cl.

| | |
|---|---|
| *C08K 3/04* | (2006.01) |
| *C07D 307/52* | (2006.01) |
| *C07C 225/06* | (2006.01) |
| *C07C 227/14* | (2006.01) |
| *C07D 207/448* | (2006.01) |
| *C07D 405/14* | (2006.01) |
| *C07F 9/38* | (2006.01) |
| *C08J 3/24* | (2006.01) |
| *C08K 3/22* | (2006.01) |
| *C08K 7/06* | (2006.01) |
| *C08K 9/04* | (2006.01) |

(52) U.S. Cl.
CPC .......... *C07D 307/52* (2013.01); *C07C 225/06* (2013.01); *C07C 227/14* (2013.01); *C07D 207/448* (2013.01); *C07D 405/14* (2013.01); *C07F 9/3813* (2013.01); *C08J 3/242* (2013.01); *C08K 3/04* (2013.01); *C08K 3/041* (2017.05); *C08K 3/042* (2017.05); *C08K 3/22* (2013.01); *C08K 7/06* (2013.01); *C08K 9/04* (2013.01); *C08J 2300/00* (2013.01); *C08J 2323/12* (2013.01); *C08J 2363/00* (2013.01); *C08J 2367/00* (2013.01); *C08K 2003/2275* (2013.01); *C08K 2201/01* (2013.01)

(58) Field of Classification Search
CPC ...... C07D 307/52; C07D 405/14; C08J 3/242; C08K 9/04
See application file for complete search history.

(56) References Cited

U.S. PATENT DOCUMENTS

| | | |
|---|---|---|
| 2010/0143701 A1 | 6/2010 | Zhu et al. |
| 2015/0210813 A1 | 7/2015 | Arai et al. |

FOREIGN PATENT DOCUMENTS

| | | |
|---|---|---|
| CN | 102867740 | 8/2015 |
| WO | 2014201603 | 12/2014 |
| WO | WO2015112958 | 7/2015 |
| WO | WO2015113023 | 7/2015 |

OTHER PUBLICATIONS

Quintana et al., "Organic Functionalization of Graphene in Dispersions", "Accounts of chemical research", Aug. 8, 2012, pp. 138-148, vol. 1, No. 46, Publisher: American Chemical Society.
Stair et al., "Non-Destructive Characterization of Ply Orientation and Ply Type of Carbon Fiber Reinforced Laminated Composites", "Department of Mechanical Engineering", , Publisher: Baylor University, Published in: Waco, TX.

*Primary Examiner* — Hannah J Pak
(74) *Attorney, Agent, or Firm* — Davis, Brown, Koehn, Shors & Roberts, P.C.; Sean D. Solberg

(57) ABSTRACT

Disclosed is a non-destructive universal method of functionalization of graphitic carbonaceous materials that enables their alignment, cross-linking, and effective integration into composite materials.

19 Claims, 4 Drawing Sheets

SEM images of carbon fibers before (top) and after (bottom) functionalization with flakes of maleic anhydride-functionalized graphene

VERSATILE NON-DESTRUCTIVE SURFACE MODIFICATION OF CARBONACEOUS MATERIALS AND PROCESS FOR GRAFTING INTO POLYMER MATRICES

CROSS REFERENCE TO RELATED APPLICATION(S)

This application claims priority to U.S. Provisional Application No. 62/268,657 that was filed on Dec. 17, 2015, which is hereby incorporated by references in its entirety.

BACKGROUND OF THE INVENTION

Graphene, carbon nanotubes, and other carbonaceous materials have received increased attention for their various applications in materials chemistry, such as mechanically enforcing elements of plastics, components of light converting devices, drug delivery systems, and catalysis. It is well-known that the traditional functionalization of bulk carbon by oxidation is destructive. It has also been previously understood that the reactivity of bulk carbon is too low to be functionalized by the known non-destructive [2+3] dipolar addition of N-alkylglycine and aldehydes or Diels-Alder addition. As described herein, the inventors have unexpectedly found that the mild procedures of functionalization, previously used in fullerenes, graphene, carbon nanofibers, and carbon nanotubes, can be applied to much less reactive bulk carbon, such as carbon fibers, and enable cross-linking by introducing the furan functional group to the surface of carbonaceous materials.

BRIEF SUMMARY OF THE INVENTION

The present invention relates to versatile, non-destructive methods of functionalization of graphitic carbonaceous materials that enables their alignment, cross-linking, and effective integration into composite materials. The methods are based on the [2+3] dipolar addition, Diels-Alder addition, or π-stacking interaction with the π-electron system of the graphitic basal plane. Neither interaction breaks any carbon-carbon bonds, which preserves the structural integrity of the carbonaceous component that is responsible for the enhanced mechanical strength of the composite material.

The methods comprise preparing a carbonaceous material, the functionalization of the prepared material with a linker, optionally the re-functionalization of the linker with the desired functional groups, and optionally the addition of a cross-linking reagent at the moment of impregnation of the carbonaceous component to the composite material. The present invention is superior to prior known methods, resulting in improved mechanical performance by better adhesion, alignment, and cross-linking. The introduced functional groups provide an opportunity to repair the polymer molecules damaged by ozone or ions and, therefore, may increase resistance of the composite material to radiation.

DETAILED DESCRIPTION OF THE INVENTION

Figure 1:
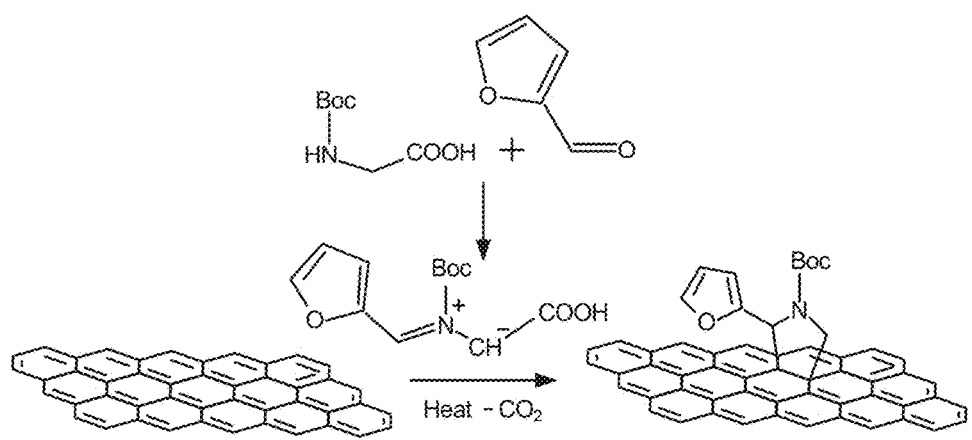
FIG. 1 depicts the functionalization of carbons by [2+3] dipolar addition, according to exemplary embodiments.
Figure 2:
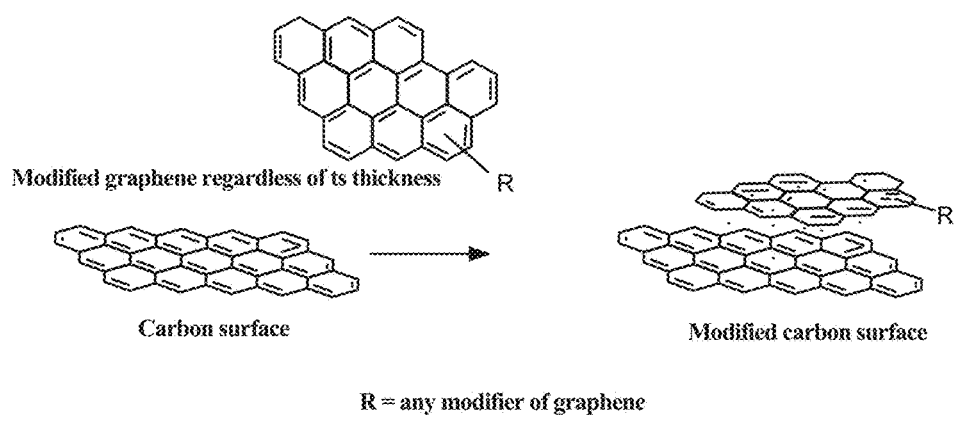
FIG. 2 depicts the functionalization of carbons by π-π stacking interaction, according to exemplary embodiments.
Figure 3:
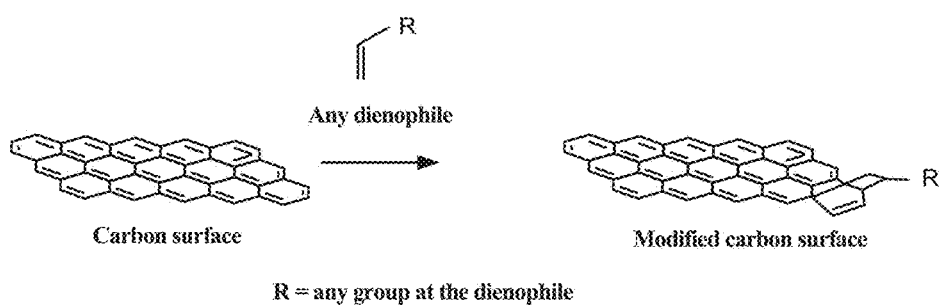
FIG. 3 depicts the functionalization of carbons by Diels-Alder addition, according to exemplary embodiments.

As used herein, the singular forms "a," "an," and "the" include plural referents unless the context clearly dictates otherwise. Thus, for example, reference to "a functional group" refers to one or more functional groups, and reference to "the method" includes reference to equivalent steps and methods that would be understood and appreciated by those skilled in the art, and so forth.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

The instant disclosure relates to non-destructive universal methods of functionalization of graphitic carbonaceous materials that enable their alignment, cross-linking, and effective integration into composite materials. These methods are based on the [2+3] dipolar addition, Diels-Alder, or π-stacking interaction with the π-electron system of the graphitic basal plane. Neither interaction breaks any carbon-carbon bonds, which preserves structural integrity of the carbonaceous component that is responsible for the enhanced mechanical strength of the composite material.

It is generally understood by skilled artisans that the simple addition of carbon nanotubes or graphene to industrial polymers will enhance the mechanical strength of the material [1,2]. It is further understood that the introduction of carboxy-, epoxy-, and other functional groups to the surface of carbonaceous materials by oxidation enables their covalent grafting by the molecular moieties that improve the integration of the carbonaceous component into the composite material [3]. These applications are limited, however, by the fact that the oxidation of the carbon damages the graphene sheets, which compromises the structural integrity of the mechanically robust sp2-carbon network. In other words, the oxidation of the carbon groups reduces the ability to increase the mechanical strength of the composite material.

On the other hand, the non-destructive [2+3] dipolar addition of N-alkylated glycine and an aldehyde to C=C bonds of graphitic materials allows for their functionalization by organic functional groups [4-7]. Typically, such a reaction is carried out with rather expensive Boc-protected PEG-derivatives of glycine. Carbon nanofibers can also be functionalized by Diels-Alder addition of 1,3-butadiene [7]. However, these methods have traditionally been limited to use with fullerenes, carbon nanotubes, and nanofibers, where the chemical activity is enhanced by the surface curvature.

The inventors have overcome the limitations of these prior methods and have identified for the first time versatile non-destructive methods that do not break any carbon-carbon bonds and therefore preserve the structural integrity of the enforcing carbon fibers.

The methods disclosed herein comprise the preparation of a carbonaceous material, the functionalization of the prepared material with a linker, optionally the refunctionalization of the linker with the desired functional groups, and optionally the addition of a cross-linking reagent at the moment of impregnation of the carbonaceous component to the composite material.

One aspect of the instant disclosure relates to a method with at least two steps, wherein a first step includes the preparation (also referred to herein as "activation") of the carbonaceous material, and more specifically, the preparation activates the surface of the carbonaceous material by its treatment with solvents, ultrasound, heat, or microwave radiation. In a second step, the functionalization by the [2+3] dipolar addition is achieved by treating the carbonaceous material with a linker (a combination of glycine or N-substituted glycine, an aldehyde, and a solvent if necessary) under heating, mechanical pressure, ultrasound, microwave radiation, or combinations thereof. The functionalization by the Diels-Alder addition is achieved by treating the carbonaceous material with a dienophile linker (and a solvent if necessary) under heating, mechanical pressure, ultrasound, microwave radiation, or combinations thereof.

In at least one embodiment, the functionalization by the π-stacking interaction is achieved by the treatment of the carbonaceous material with functionalized graphene, and optionally, a solvent under room temperature, heating, mechanical pressure, ultrasound, microwave radiation, or combinations of thereof.

For the purposes of the instant disclosure, a "functional group" includes but is not limited to negatively charged groups (carboxylate, phosphonate), positively charged groups (ammonium), magnetic groups (particles of magnetite), groups enhancing integration of the carbonaceous component to the composite material (alkyl chains, monomers, oligomers, polymers), or groups enabling cross-linking (furan, carboxy-groups, hydroxy-groups, amino-groups). The functional groups can be introduced to the carbonaceous material either as a part of the linker, or at the step of refunctionalization. In at least one embodiment, the functional group is the furano-group. In an alternative embodiment, paraform is used instead of furfural.

As it will be appreciated by one of ordinary skill in the art, for purposes of the instant disclosure, a "cross-linking reagent" includes, but is not limited to:
 a. (1,6-di-(N-maleimido)hexane) that covalently tethers particles of the functionalized carbonaceous component in the composite material, by the Diels-Alder reaction with the furan functional group or with 1,3-diene domains of the graphitic structures under elevated temperatures and mechanical pressures inherent to the impregnation process;
 b. a diamine or polyamine, diol, or polyol that reacts with carboxy-groups of the functionalized carbonaceous component in the composite material under elevated temperatures and mechanical pressures inherent to the impregnation process; or
 c. a dicarboxylic acid that reacts with amino-groups or carboxy-groups of the functionalized carbonaceous component in the composite material under elevated temperatures and mechanical pressures inherent to the impregnation process.

Another aspect of the instantly disclosed methods relates to utilizing the [2+3] dipolar addition or Diels-Alder addition for functionalization of poorly reactive, or non-reactive, bulk carbonaceous materials, such as carbon fibers, to an array of activation methods such as sonication, treatment with microwave radiation, or pressure-induced mechanoactivation, which allows for functionalization in a non-toxic, inexpensive, and safe water solvent.

In at least one embodiment, the activation is accomplished by mechanoactivation. As will be appreciated by a person skilled in the art, mechanoactivation may be accomplished by way of mechanical pressure or ball milling and other methods well known in the art.

According to certain further embodiments, the activation is accomplished by ultrasound. In exemplary embodiments, ultrasound is provided at frequency from about 20,000 to about 100,000 Hz.

In a further embodiment, the activation is accomplished by microwave radiation. According to certain exemplary embodiments activation is accomplished through the application of microwave radiation an intensity of between about 0.1 to about 10,000 watts per gram of material. In these embodiments, microwave radiation is applied for at least one minute.

According to further embodiments, the activation of carbonaceous materials is accomplished through the application of at least one solvent and heat. In certain exemplary embodiments, the heat applied is between about 100° C. and about 800° C. According to still further embodiments, activation occurs at about 500° C. In certain embodiments, heat is provided in amount sufficient to induce pyrolysis in the carbonaceous materials.

In another embodiment, the [2+3] dipolar addition is performed in a non-toxic, safe, and inexpensive medium. In at least one embodiment, the addition is performed in a water-based solvent. In alternative embodiments, polymerizing aqueous solutions of acrylic acid, bis-acrylimide, and combinations thereof are used for cross-linking of carbons functionalized with the furano-group.

Another aspect of the disclosed method provides for cheaper alternatives, such as N-substituted glycine derivatives such as, 2-hydroxyethlaminoacetic acid, glyphosate, or 3-acetamidopropylaminoacetic acid, as replacements for the commonly used Boc-protected PEG-derivatives of glycine.

In certain aspects, disclosed is a method of modifying the surface of carbonaceous materials by activating the surface of a plurality of carbon fibers by sonicating the fibers in a solvent; functionalizing the activated carbon fiber by heating in a solvent with (3-(acetylamino)propyl)aminoacetic acid and paraform; and refunctionalizing the functionalized carbon fibers to produce amino-functionalized carbon fibers. In further aspects, the refunctionalizing step comprises treating the functionalized carbon fibers with aqueous HCl, then with aqueous NaOH, and then with water. In yet further aspects, the activated carbon fibers are heated to between about 50° C. and about 153° C. for at least one hour. In still further aspects, the solvent is DMF.

In certain aspects, disclosed is a method of modifying the surface of carbonaceous materials comprising: activating the surface of a plurality of carbon fibers by heating under a nitrogen atmosphere; functionalizing the activated carbon fibers by heating in a solvent with (3 N-methylglycine and furfural; and cross-linking the functionalized carbon fibers with a cross-linker. According to certain aspects, the cross-linker is 1,6-di-(N-maleimido)hexane. In further aspects, the activation step provides sufficient heat to induce pyrolysis of the carbon fibers. In these embodiments, the carbon fibers are heated to between about 100° C. and about 800° C. In certain exemplary embodiments, the carbon fibers are heated to about 500° C.

While it is known that the introduction of the furan moiety to polymers enables their cross-linking by the Diels-Alder reaction with bis-maleimides (dienophiles), in another aspect of the instantly disclosed methods, the inventors have for the first time utilized the furan functionality to enable the cross-linking of carbon fibers. This is accomplished by employing furfural at the step of the [2+3] dipolar addition.

In another aspect of the disclosed method, the inventors have determined that the non-destructive functionalization of carbonaceous materials can be accomplished by their π-π-stacking interaction with functionalized nanoplatelets of graphene. In at least one embodiment, functionalized graphene is used as a linker that adheres to the graphitic carbons. In at least one embodiment, the functionalized graphene is prepared by mechanoactivated Diels-Alder addition of a dienophile to graphite coupled with its exfoliation [8].

In another aspect, the instantly disclosed methods utilize for the first time the furan-maleimide addition for cross-linking of carbon fibers or other carbonaceous components enhancing mechanical strength of composite materials. This is achieved by the novel application of the furfural component in the known general process of [2+3] dipolar addition to graphene [5].

The phenomenon of alignment of positively charged carbon nanotubes and a negatively charged metallic surface is discussed in the literature [10]. In another aspect, the instantly disclosed methods improve on this known method of alignment of carbonaceous materials in magnetic field by their conjugation with magnetic particles [11]. The instantly disclosed methods enable stronger adhesion of magnetic particles to graphitic carbonaceous materials without compromising the structural integrity of the composite material.

For instance, the non-destructive introduction of carboxy-, phosphonato-, and phenol covalent "anchors" to a carbonaceous surface improves their adhesion to the magnetic particles, and at the same time preserves the structural integrity of the carbonaceous component in the final composite material. Further still, the introduction of positively and negatively charged functional groups into the carbonaceous materials will facilitate their self-assembly into "bundles", which may enable the use of "discontinued fibers" for enhancing mechanical properties of composite materials.

The controlled self-assembly and directed alignment of carbonaceous particles can be modified by including different surface functional groups (amino-, carboxy-, carboxygrapheno-, furano-, hexadecyl-, magnetite-), particle size (ranging from multi-walled carbon nanotubes (MWCNT) to bulk carbon fibers), and the extent of particle cross-linking by 1,6-dimaleimidohexane. For instance, in at least one embodiment, paraform can be used instead of furfural. The effectiveness of self-alignment can be monitored by optical microscopy, scanning electron microscope (SEM), transmission electron microscope (TEM), and conductivity measurement by a four probe meter.

The instantly disclosed methods are versatile and the scope of potential applications is vast. By way of example, these can be used to achieve improved integration of carbonaceous materials, including from the waste stream of discontinued carbon fibers, to industrial composite materials. Additional applications exist in varied contexts, including for instance, applications where there is a desire for a material enforced by aligned, cross-linked, carbon-based fibers. The self-assembly of functionalized carbonaceous particles and their directed alignment opens the gateway for the development of major research projects aimed at the novel mechanically strong materials and magnetoactivated drug delivery systems, including research projects involving the manipulation of magnetically sensitive cross-linked gels. The introduction of antioxidant groups (such as phenols, thiols) or groups reactive with carbonyls (such as amino-, hydrazino-groups) to the carbonaceous particles provides cross-linking of plastics damaged by ozone or ionized particles and, therefore, may increase resistance of composite materials to radiation. The scope of applications for materials enforced by aligned, structurally intact, and cross-linked carbon-based fibers ranges from spaceships to dental fillings.

Throughout this disclosure, various publications, patents and published patent specifications are referenced. Where permissible, the disclosures of these publications, patents and published patent specifications are hereby incorporated by reference in their entirety into the present disclosure to more fully describe the state of the art.

Before explaining the various embodiments of the disclosure, it is to be understood that the invention is not limited in its application to the details of construction and the arrangement of the components set forth in the following description. Other embodiments can be practiced or carried out in various ways. Also, it is to be understood that the phraseology and terminology employed herein is for the purpose of description and should not be regarded as limiting the inventions described in any way.

EXAMPLES

Example 1

Preparation: Carbon fibers are pyrolized under nitrogen atmosphere (10+ min at 100-800° C. under a nitrogen atmosphere).

Functionalization: The prepared carbon fibers are heated in dimethylformamide (DMF) (110-160° C. for 24-120 hours) with N-methylglycine and furfural.

Refunctionalization: Not needed.

Cross-linking: The functionalized carbon fibers are mixed with 1,6-di-(N-maleimido)hexane, and impregnated into a melted polypropylene or epoxy-plastic.

Example 2

Preparation: Carbon fibers are sonicated (5-1000 watts per gallon, 10+ min) in DMF. Functionalization: The prepared carbon fibers are heated in DMF (50° C.-153° C., 1+ hour) with (3-(acetylamino)propyl)aminoacetic acid and paraform. (Or (6-(acetylamino)hexyl)aminoacetic acid)

Refunctionalization: The acetamido-groups are converted by amino-groups by treating the functionalized carbon fibers by aqueous HCl (0.1+M), then by aqueous NaOH (0.001+ M), and finally with water. The amino-functionalized carbon fibers are ready for impregnation to an epoxide resin.

Cross-linking: Not needed.

Example 3

Preparation: Carbon fibers are treated by microwave radiation.

Functionalization: The prepared carbon fibers are mixed with (2-hydroxyethyl)aminoacetic acid and paraform and subjected to mechanical pressure of 1,000 Pa for 1+ hours. The hydroxy-functionalized carbon fibers are ready for impregnation to a polyester plastic.

Refunctionalization: Not needed.

Cross-linking: Not needed.

Example 4

Preparation: Not needed.

Functionalization: Carbon fibers are mixed with (3-(acetylamino)propyl)aminoacetic acid, paraform, and treated by microwave radiation. (Or (6-(acetylamino)hexyl) aminoacetic acid) Refunctionalization: The acetamido-groups are converted to hydrophobic polymeric particles by treating the functionalized carbon fibers with aqueous HCl (0.1+M), then with aqueous NaOH (0.001+M), and finally with a copolymer of maleic anhydride and propene. The carbon fibers conjugated with a polymer are ready for impregnation to a plastic.

Cross-linking: Not needed.

Example 5

Preparation: Not needed.

Figure 4:
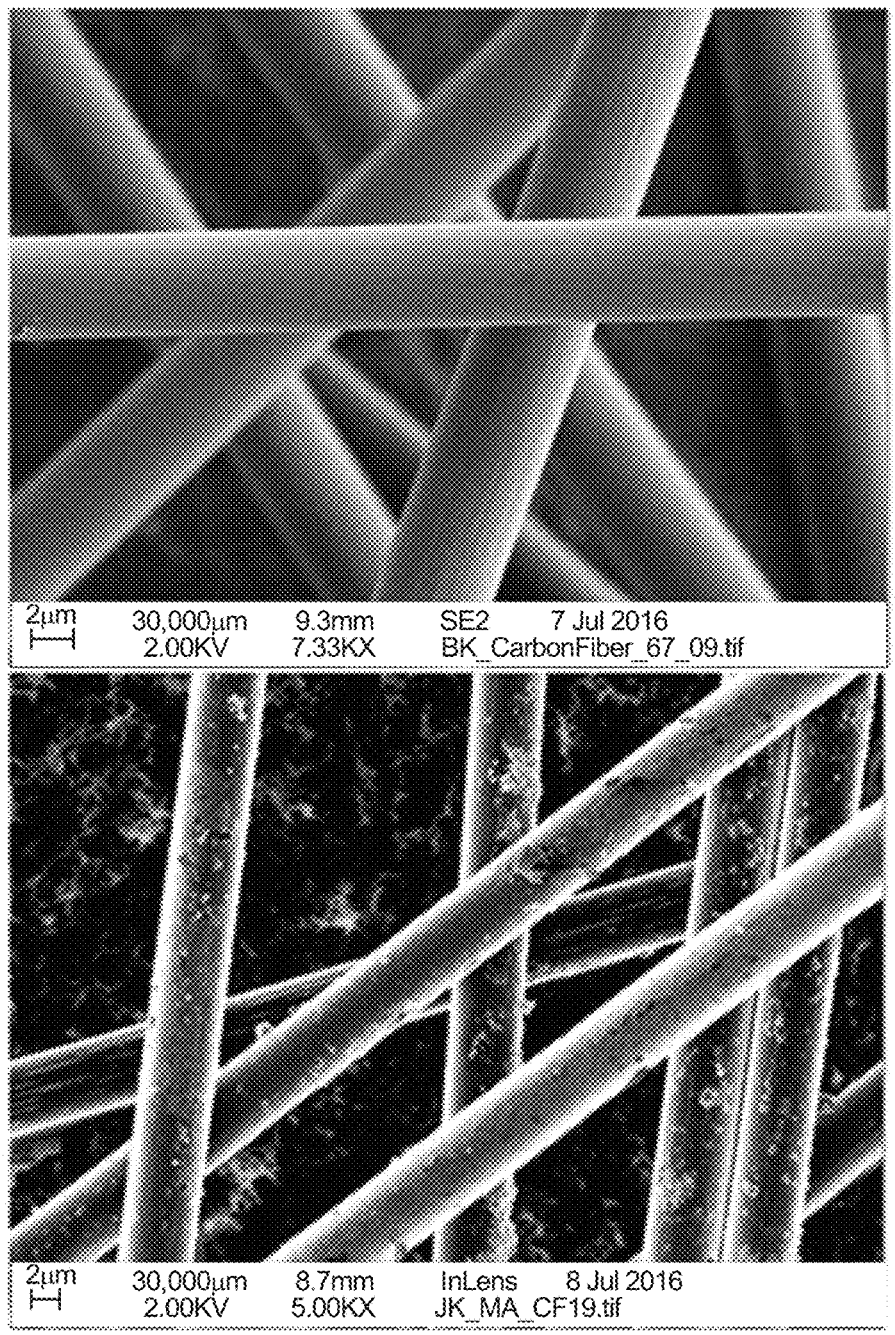
FIG. 4 depicts an exemplary S.E.M. image of carbon fibers before and after functionalization with modified grapheme, according to exemplary embodiments.

Functionalization: Carbon fibers are treated with a suspension of N-hexadecylmaleimide-functionalized graphene in DMF (or in methanol, or solvent-free by melting then pressing, see FIG. 4). The carbon fibers conjugated with a polymer are ready for impregnation to a plastic.

Refunctionalization: Not needed.

Cross-linking: Not needed.

Example 6

Preparation: Not needed.

Functionalization: Carbon nanotubes are treated with a suspension of maleic anhydride-functionalized graphene in DMF and heated under nitrogen.

Refunctionalization: The anhydride groups are converted to carboxylate-groups by the treatment with aqueous ammonia (0.001+M). Nanoparticles of magnetite ($Fe_3O_4$) are grown on the introduced carboxylate-groups by the known procedure (treatment with aqueous $FeCl_2$, $FeCl_3$, and ammonia at mechanical shaking for 24 hours). The prepared carbon nanotube-magnetite assembly is ready for the alignment in a polymer matrix by the magnetic field.

Cross-linking: Not needed.

Example 7

Preparation: Not needed.

Functionalization: Carbon fibers are mixed with maleic anhydride-functionalized graphene, and subjected to mechanical pressure of 1,000 Pa for at least one hour.

Refunctionalization: Not needed.

Cross-linking: The functionalized carbon fibers are mixed with 1,6-diaminohexane and impregnated into a melted plastic.

Example 8

Preparation: Not needed.

Functionalization: An aqueous suspension of carbon nanotubes, glyphosate, and 3,4-dehydroxybenzaldehyde are refluxed under sonication.

Refunctionalization: Nanoparticles of magnetite ($Fe_3O_4$) are grown on the introduced phosphate- and catechol-groups by the known treatment with aqueous $FeCl_2$, $FeCl_3$, and ammonia (mechanical shaking for 24 hours). The prepared carbon nanotube-magnetite assembly is ready for the alignment in a polymer matrix by the magnetic field.

Cross-linking: Not needed.

Example 9

Preparation: Not needed.

Functionalization: Carbon fibers are mixed with melted N-hexadecylmaleimide (the weight carbon fibers:N-hexadecylmaleimide ratio is 1000:1 to 1:100), and cooled to room temperature. The solidified "bark" is ready for impregnation to a plastic.

Refunctionalization: Not needed.

Cross-linking: Not needed.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

REFERENCES CITED

1. Gong, X.; Liu, J.; Baskaran, S.; Voise, R.; Young, J. Surfactant-assisted processing of carbon nanotube/polymer composites. Chem. Mater. 2000, 12, 1049-1052
2. Stankovich, S.; Dikin, D.; Dommett, G.; Kohlhaas, K.; Zimney, E.; Stach, E.; Piner, R.; Nguyen, S.; Ruoff, R. Graphene-based composite materials. Nature 442, 282-286
3. Lefrant, S.; Baibarac, M.; Baltog, I. Raman and FTIR-spectroscopy as valuable tools for the characterization of polymer and carbon nanotube based composites. J. Mat. Chem. 2009, 19, 5690-5704
4. Quintana, M.; Spyrou, K.; Grzekzak, M.; Browne, W.; Rudolf, P.; Prato, M. Functionalization of graphite via 1,3-dipolar addition. ACS NANO 2010, 4, 6, 3527-3533
5. Georgakilas, V.; Bourlinos, A.; Zboril, R.; Steriotis, Th.; Dallas, P.; Stubos, A.; Trapalis, Ch. Organic functionalisation of graphenes. Chem Comm. 2010, 46, 1766-1768
6. Zakharian, T.; Christianson, D. Design and synthesis of C60-benzenesulfonamide conjugate. T. Lett. 2010, 51, 3645-3648.
7. Paiva, M.; Novais, R.; Araujo, R.; Pederson, K.; Proenca, M.; Silva, C.; Costa, C.; Lanceros-Mendez, S. Organic functionalization of carbon nanofibers for composite applications. 2010, 31,3, 369-376
8. Seo, J.; Jeon, I.; Baek, J. Mechanochemically driven solid-state Diels-Alder reaction of graphite into graphene nanoplatelets. Chem. Sci. 2013, 4, 4273-4277
9. Okhay, N.; Jegat, C.; Mignard, N.; Taha, M. PMMA thermoreversible networks by Diels-Alder reaction. Reactive & Functional Polymers 73 (2013) 745-755
10. Hwang, J.; Eltohamy, M.; Kim, H.; Shin, U. Self assembly of positively charged carbon nanotubes with oppositely charged metallic surface. Appl. Surf. Sci. 2012, 258, 6455-6459

11. Hong, H.; Luan, X.; Horton, M.; Li, Ch.; Peterson, G. Alignment of carbon nanotubes comprising magnetically sensitive metal oxides in heat transfer nanofluids. Thermochim. Acta 2011, 525, 87-92

We claim:

1. A non-destructive method of modifying the surface of carbonaceous materials comprising:
   activating the surface of the carbonaceous materials; and
   functionalizing the activated surface of the carbonaceous materials through treatment with a linker to create a [2+3] dipolar addition,
   wherein the linker comprises a combination of (a) glycine, N-substituted glycine, or a combination thereof and (b) an aldehyde.

2. The method of claim 1, wherein the activating the surface of the carbonaceous material is by way of treatment with at least one solvent, ultrasound, heat, microwave radiation, or combinations thereof.

3. The method of claim 2, wherein activating the surface of the carbonaceous materials is by way of treatment of the materials with at least one solvent and ultrasound.

4. The method of claim 3 wherein ultrasound is applied at a frequency of between about 20,000 and about 100,000 Hz, at a power of between about 5 and about 1,000 watts per gallon, and for a duration of at least 10 minutes.

5. The method of claim 1, wherein the linker further comprises a solvent.

6. The method of claim 1, wherein the functionalization is achieved under heating, mechanical pressure, ultrasound, microwave radiation, or combinations thereof.

7. The method of claim 1, further comprising a re-functionalization step.

8. The method of claim 1, further comprising a step of adding a cross-linking reagent.

9. The method of claim 8, wherein the cross-linking reagent is 1,6-di-(N-maleimido) hexane.

10. The method of claim 8, wherein the cross-linking reagent is a diamine or polyamine, diol, or polyol.

11. The method of claim 8, wherein the cross-linking reagent is a dicarboxylic acid.

12. A method of modifying the surface of carbonaceous materials comprising:
   a. activating the surface of a plurality of carbon fibers by sonicating the carbon fibers in a solvent;
   b. functionalizing the activated carbon fibers by heating in the solvent with 3-(acetylamino)propyl-aminoacetic acid and paraform; and
   c. refunctionalizing the functionalized carbon fibers to produce amino-functionalized carbon fibers.

13. The method of claim 12, wherein the refunctionalizing step comprises treating the functionalized carbon fibers with aqueous HCl, then with aqueous NaOH, and then with water.

14. The method of claim 12, wherein the activated fibers are heated in the solvent to between about 50° C. and about 153° C. for at least one hour.

15. The method of claim 14 wherein the solvent is DMF.

16. A method of modifying the surface of carbonaceous materials comprising:
   a. activating the surface of a plurality of carbon fibers by heating under a nitrogen atmosphere;
   b. functionalizing the activated carbon fibers by heating in a solvent with 3 N-methylglycine and furfural; and
   c. cross-linking the functionalized carbon fibers with a cross-linker.

17. The method of claim 16 wherein the cross-linker is 1,6-di-(N-maleimido)hexane.

18. The method of claim 16, wherein the activation step a. provides sufficient heat to induce pyrolysis of the carbon fibers.

19. The method of claim 18 wherein the carbon fibers are heated to between about 100° C. and about 800° C.

* * * * *